United States Patent
Kang

(10) Patent No.: US 11,540,862 B2
(45) Date of Patent: Jan. 3, 2023

(54) RECOVERY DEVICE AND METHOD FOR RECOVERING MAGNETIC PARTICLE

(71) Applicant: BOE TECHNOLOGY GROUP CO., LTD., Beijing (CN)

(72) Inventor: Jingang Kang, Beijing (CN)

(73) Assignee: Beijing BOE Technology Development Co., Ltd., Beijing (CN)

( * ) Notice: Subject to any disclaimer, the term of this patent is extended or adjusted under 35 U.S.C. 154(b) by 1080 days.

(21) Appl. No.: 16/303,585

(22) PCT Filed: Mar. 22, 2018

(86) PCT No.: PCT/CN2018/080078
§ 371 (c)(1),
(2) Date: Nov. 20, 2018

(87) PCT Pub. No.: WO2018/228015
PCT Pub. Date: Dec. 20, 2018

(65) Prior Publication Data
US 2021/0052304 A1    Feb. 25, 2021

(30) Foreign Application Priority Data
Jun. 14, 2017    (CN) .......................... 201710454560.8

(51) Int. Cl.
*A61B 17/52*    (2006.01)
*A61F 9/007*    (2006.01)

(52) U.S. Cl.
CPC .......... *A61B 17/52* (2013.01); *A61F 9/00709* (2013.01); *A61B 2217/005* (2013.01)

(58) Field of Classification Search
CPC ............... A61B 17/52; A61B 2217/005; A61F 9/00709; A61F 9/00736
See application file for complete search history.

(56) References Cited

U.S. PATENT DOCUMENTS 2,801,628 A * 8/1957 Pape ...................... A61B 17/52
                                                                600/11
4,240,410 A * 12/1980 Pickering ............... A61B 17/52
                                                                600/11
(Continued)

FOREIGN PATENT DOCUMENTS

AU    2014228563 A1    10/2015
CA       2906296 A1     9/2014
(Continued)

OTHER PUBLICATIONS

Chinese Office Action dated Nov. 5, 2018, from application No. 201710454560.8.
(Continued)

*Primary Examiner* — Carrie R Dorna
(74) *Attorney, Agent, or Firm* — Arch & Lake LLP

(57) ABSTRACT

The present disclosure provides a recovery device and a method for recovering a magnetic particle. The recovery device includes a main pipe, a needle tube, and a suction power mechanism. The needle tube is connected to a first end of the main pipe, and a terminal of the needle tube is magnetic for adsorbing a magnetic particle to the terminal of the needle tube. The suction power mechanism is configured to absorb the magnetic particle attached on the terminal of the needle tube into the main pipe. The present disclosure utilizes a magnetic needle tube to implement adsorption of the magnetic particle while the magnetic particle is absorbed into the main pipe by an absorption power mechanism, thus achieving recovering of the magnetic particle.

15 Claims, 2 Drawing Sheets

(56) References Cited

U.S. PATENT DOCUMENTS

| | | |
|---|---|---|
| 8,830,648 B2 | 9/2014 | Abbott et al. |
| 9,775,968 B2 | 10/2017 | Novak |
| 2008/0188877 A1 | 8/2008 | Hickingbotham |
| 2011/0060320 A1 | 3/2011 | Aharon-Attar |
| 2013/0253402 A1* | 9/2013 | Badawi .............. A61F 9/00736 604/8 |
| 2013/0303847 A1 | 11/2013 | Sitti et al. |
| 2014/0052020 A1* | 2/2014 | Allen .................... A61B 17/52 600/562 |
| 2014/0128771 A1* | 5/2014 | LaConte ........... A61B 10/0283 600/566 |
| 2014/0236163 A1* | 8/2014 | Olson ................. A61F 2/1662 606/107 |
| 2014/0276899 A1 | 9/2014 | Novak |
| 2015/0202082 A1 | 7/2015 | Ilios et al. |
| 2018/0021547 A1 | 1/2018 | Novak |

FOREIGN PATENT DOCUMENTS

| | | |
|---|---|---|
| CN | 1583185 A | 2/2005 |
| CN | 1774203 A | 5/2006 |
| CN | 1944003 A | 4/2007 |
| CN | 101083961 A | 12/2007 |
| CN | 101220894 A | 7/2008 |
| CN | 101346112 A | 1/2009 |
| CN | 103037762 A | 4/2013 |
| CN | 103052367 A | 4/2013 |
| CN | 203943800 U | 11/2014 |
| CN | 107049594 A | 8/2017 |
| WO | WO-2014/036437 A1 | 3/2014 |
| WO | WO-2014/143550 A1 | 9/2014 |

OTHER PUBLICATIONS

International Search Report and Written Opinion dated May 30, 2018, from application No. PCT/CN2018/080078.
Chinese Office Action dated Jun. 4, 2019, from application No. 201710454560.8.

* cited by examiner

RECOVERY DEVICE AND METHOD FOR RECOVERING MAGNETIC PARTICLE

CROSS REFERENCE

This application is based upon International Application No. PCT/CN2018/080078, filed on Mar. 22, 2018, which claims priority to Chinese Patent Application No. 201710454560.8, filed on Jun. 14, 2017, the entire contents thereof are incorporated herein by reference.

TECHNICAL FIELD

The present disclosure relates to the field of magnetic particle technology, and in particular to a recovery device and a method for recovering a magnetic particle.

BACKGROUND

Vitreous opacity is a common clinical problem, the most common cause is posterior vitreous detachment. The treatment of vitreous opacity by taking drugs or using eye drops hardly has any effect. Current treatments include laser vitreous ablation and vitrectomy. Laser vitreous ablation is effective in removing large vitreous floating objects, but there is also a potential risk of damage to the macula or lens. Vitrectomy, or minimally invasive vitrectomy, generally removes about 90% of the vitreous and fills in the vitreous with substitute material. The vitrectomy can be done under smaller incisions, and the wound does not need to be sutured. The foreign body sensation of the posterior eye can be reduced, and the risk of ocular complications such as retinal tears and retinal detachment can also be reduced. Minimally invasive vitrectomy is currently considered the best choice for the treatment of vitreous opacity.

However, whether it is a vitreous substitute for gas or liquid that is currently widely used in clinical practice, or a hydrogel or capsular vitreous substitute in the experimental stage, there are specific indications, and there are various disadvantages. In addition, studies in the field have shown that the incidence of cataract after vitrectomy is as high as 22.5%-60%.

Those skilled in the art are working to develop a micro-robot system that can be used for eye surgery. The robot is a tiny magnetic particle, that is, a micro-magnetic robot with a size of an order less than millimeters. In surgery, the micro-magnetic robot may be injected into the vitreous body to provide power and fine motion control for the micro-magnetic robot through a corresponding external magnetic field device.

In order to enable the above-mentioned micro-magnetic robot-based design to be applied to practical use as early as possible, for example, for the treatment of vitreous opacity, the placement, control, operation, of the above-described micro-magnetic robot are urgent and important technical issues that need to be solved by those skilled in the art.

SUMMARY

According to one aspect of the present disclosure, there is provided a recovery device for recovering a magnetic particle. The recovery device includes a main pipe, a needle tube, and a suction power mechanism. The needle tube is connected to a first end of the main pipe, and a terminal of the needle tube facing away from the main pipe is magnetic for adsorbing a magnetic particle to the terminal of the needle tube. The suction power mechanism is configured to absorb the magnetic particle attached on the terminal of the needle tube into the main pipe.

According to an arrangement of the present disclosure, the needle tube is integrally formed with the main pipe.

According to an arrangement of the present disclosure, the material of the main pipe includes a non-metal material.

According to an arrangement of the present disclosure, the material of the main pipe includes a transparent material.

According to an arrangement of the present disclosure, the material of the main pipe includes a non-metal and transparent material.

According to an arrangement of the present disclosure, the material of the needle tube includes a metal material.

According to an arrangement of the present disclosure, the material of the terminal of the needle tube is a permanent magnet metal.

According to an arrangement of the present disclosure, the material of the needle tube includes a metal material, and the material of the terminal of the needle tube includes a permanent magnet metal material.

According to an arrangement of the present disclosure, the needle tube has a diameter less than or equal to 1 mm.

According to an arrangement of the present disclosure, the portion of the main pipe proximate to the first end is substantially in a curved shape such as, for example, a gooseneck-like or arc shape.

According to an arrangement of the present disclosure, the suction power mechanism includes an air pressure adjusting device; the air pressure adjusting device is connected to a second end of the main pipe, and the air pressure adjusting device is configured to cause the magnetic particle to enter the main pipe by applying a negative pressure in the main pipe.

According to an arrangement of the present disclosure, the recovery device further includes a recovering container. The recovery container is connected to the main pipe and disposed between the first end and the second end of the main pipe for accommodating the magnetic particle when the magnetic particle enters the main pipe.

According to an arrangement of the present disclosure, the recovery device further includes an electromagnetic device. The electromagnetic device is disposed on the main pipe to form a magnetic field in the main pipe to provide a moving force to the magnetic particle in the main pipe.

According to an arrangement of the present disclosure, the recovery device further includes a recovery container and an electromagnetic device. The recovery container is connected to the main pipe and disposed between the first end and the second end of the main pipe for accommodating the magnetic particle when the magnetic particle enters the main pipe; and the electromagnetic device is disposed on the main pipe to form a magnetic field in the main pipe to provide a moving force to the magnetic particle in the main pipe.

According to an arrangement of the present disclosure, the electromagnetic device includes at least an electromagnetic coil; and the electromagnetic coil is disposed around the outer circumference of the main pipe.

According to an arrangement of the present disclosure, the electromagnetic device is disposed between the first end of the main pipe and the recovery container.

According to an arrangement of the present disclosure, the suction power mechanism includes an air pressure adjusting device. The air pressure adjusting device is connected to a second end of the main pipe, and the air pressure adjusting device is configured to cause the magnetic particle to enter the main pipe by applying a negative pressure in the main pipe. The recovery device further includes a recovery container and an electromagnetic device. The recovery container is connected to the main pipe and disposed between the first end and the second end of the main pipe for accommodating the magnetic particle when the magnetic particle enters the main pipe. The electromagnetic device is disposed on the main pipe to form a magnetic field in the main pipe to provide a moving force to the magnetic particle in the main pipe.

According to another aspect of the present disclosure, there is provided a method for recovering a magnetic particle by a recovery device. The recovery device includes a main pipe.

The recovery device includes a needle tube connected to a first end of the main pipe, and a terminal of the needle tube away from the main pipe is magnetic for adsorbing the magnetic particle to the terminal of the needle tube.

The recovery device includes a suction power mechanism configured to absorb the magnetic particle attached on the terminal of the needle tube into the main pipe.

The method for recovering a magnetic particle includes:

placing at least a part of the needle tube in a working environment of a magnetic particle. The magnetic particle is to be adsorbed by the terminal of the needle tube. The method includes absorbing the magnetic particle into the main pipe by the suction power mechanism.

According to an arrangement of the present disclosure, the method for recovering a magnetic particle further includes:

forming a magnetic field by an electromagnetic device. The magnetic particle is controlled to move in the main pipe by the action of the magnetic field. The method includes connecting a recovery container to the main pipe. When the magnetic particle enters the main pipe, the magnetic particle is moved to the recovery container for storage.

DETAILED DESCRIPTION

Figure 1:
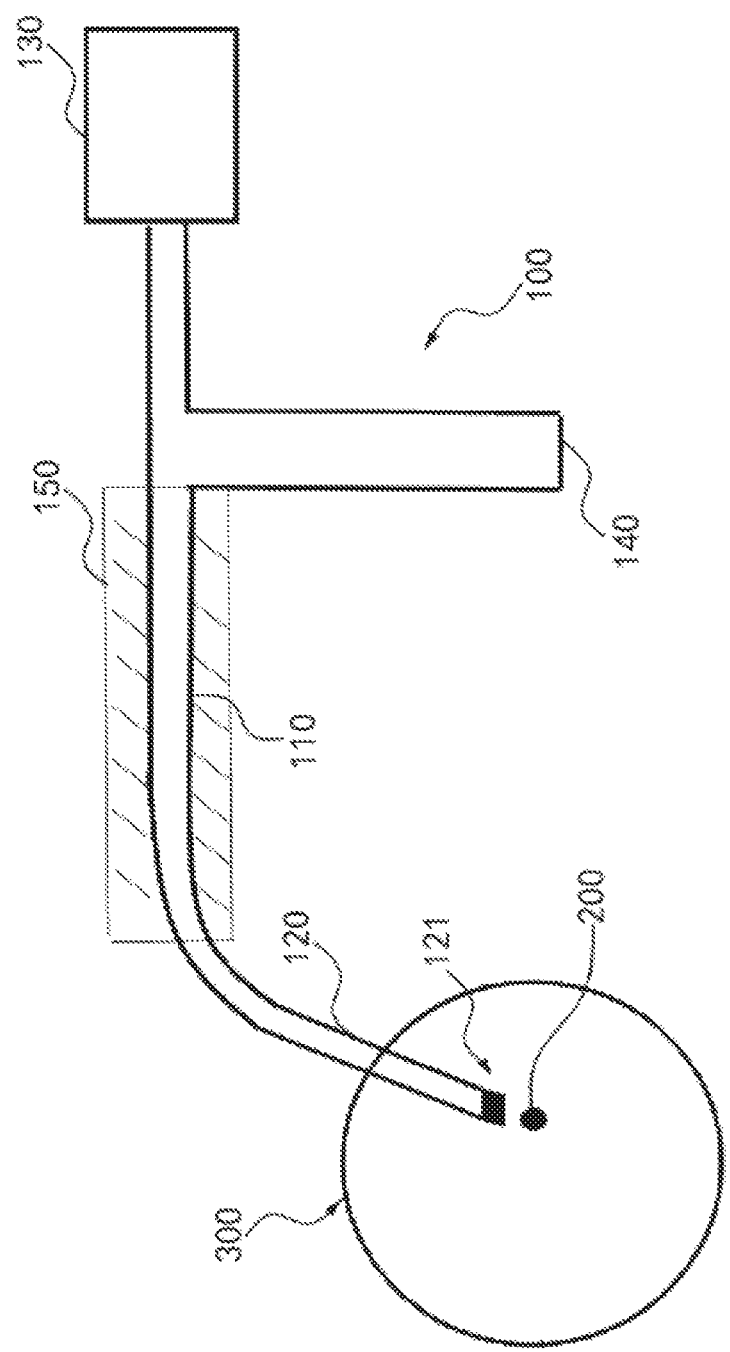
FIG. 1 is a schematic diagram of a recovery device according to an exemplary arrangement.

The same reference numerals in the drawings denote the same or similar structures, and thus their detailed description will be omitted. Example arrangements will now be described more fully with reference to the accompanying drawings. However, the example arrangements can be embodied in a variety of forms, and should not be construed as being limited to the arrangements set forth herein. Rather, these arrangements are provided so that this disclosure will be thorough and complete, and convey the concepts of the example arrangements to those skilled in the art.

Referring to FIG. 1, FIG. 1 is a schematic diagram of a recovery device 100 according to an exemplary arrangement, illustrating the principles of the present disclosure. In the exemplary arrangement, the recovery device 100 provided by the present disclosure is exemplified by a recovery device 100 of a recovering magnetic robot, and further, exemplified by a recovery device 100 for recovering a magnetic particle 200 (for example, a micro magnetic robot) in the vitreous body 300. It will be readily understood by those skilled in the art that in order to use the recovery device 100 provided by the present disclosure for recovering other types of magnetic robots, or for recovering magnetic robots from other working environments, various modifications, additions, substitutions, deletions, or other changes may be made to the arrangements described below, all of which are still within the scope of the principles of the recovery device 100 provided by the present disclosure.

As shown in FIG. 1, in the present arrangement, the recovery device 100 provided by the present disclosure can be used to recover the magnetic fine particle 200 from the vitreous body 300 of the human eye. Wherein the recovery device 100 mainly includes a main pipe 110, a needle tube 120 and a suction power mechanism. The suction power mechanism may be an air pressure adjusting device 130, and the recovery device further includes a recovery container 140, and an electromagnetic device. The structure, connection relationship and function of the main components of the recovery device 100 provided by the present disclosure will be described in detail below with reference to the accompanying drawings.

As shown in FIG. 1, in the present arrangement, the main pipe 110 has a first end and a second end. The first end is connected to the needle tube 120 and the second end is connected to the air pressure adjusting device 130.

As shown in FIG. 1, in the present arrangement, in order to adapt to the operation of the vitreous body 300 of the human eye as the working environment of the magnetic micro particles 200, the portion of the main pipe 110 proximate the first end may be substantially in a curved shape such as a gooseneck-like or arc shape, but not limited thereto. In order to smoothly transport the magnetic particles into the main pipe, the needle tube 120 can be a straight tube which is transitionally connected to the main pipe, but not limited thereto, the needle tube 120 can also be an arc tube.

Furthermore, in the present arrangement, the material of the main pipe 110 may preferably be non-metal, based on the recycling object being the magnetic robot and considering the arrangement and operation principle of the electromagnetic coil 150 (described in detail later). In addition, in order to facilitate the operator to observe the situation in the main pipe 110, for example, to observe the moving state of the magnetic particle 200 in the main pipe 110, the material of the main pipe 110 may preferably be a transparent material. Further, in the present arrangement, the material of the main pipe 110 may be a non-metallic transparent material.

It should be noted that the specific shape, structure and material of the main pipe 110 may be flexibly adapted when the object to be recovered is changed from a magnetic robot to another type of component, or the working environment of the object to be recovered is changed from a liquid environment such as the vitreous body 300 to another type of environment.

As shown in FIG. 1, in the present arrangement, the needle tube 120 is connected to the first end of the main pipe 110, and the terminal 121 of the needle tube 120 away from the main pipe 110 is magnetic. With the magnetic terminal 121, the needle tube 120 can adsorb the magnetic particle 200 in the vitreous body 300 to the terminal 121 of the needle tube 120 after being placed in the vitreous body 300. In one arrangement, the needle tube can be integrally formed with the main pipe, and also can be connected to the main pipe detachable, which is not limited thereto.

In the present arrangement, considering the size of the magnetic particle 200 and the operational requirement of the vitreous body 300 as the working environment, the diameter of the needle tube 120 is slightly larger than the size of the magnetic particle 200, for example, less than or equal to 1 mm. It should be noted that since the size is small, the thickness of the wall of the needle tube 120 is not considered in the description of the present arrangement, and the diameter can be understood as the inner diameter of the needle tube 120.

Furthermore, in the present arrangement, in order to achieve adsorption of the magnetic particle 200 by the needle tube 120, the material of the terminal 121 of the needle tube 120 may preferably be a permanent magnet metal, and the material of the needle tube 120 may be metal. In other arrangements, the needle tube 120 may also be made from other materials, but it is necessary to ensure that the terminal 121 has magnetic properties to perform adsorption of the magnetic particle 200.

As shown in FIG. 1, in the present arrangement, the air pressure adjusting device 130 is connected to the second end of the main pipe 110. By adjusting the air pressure in the main pipe 110 and the needle tube 120, the air pressure adjusting device 130 can apply an instantaneous negative pressure in the main pipe 110 and the needle tube 120, so that the magnetic particle 200 adsorbed at the terminal 121 of the needle tube 120 may pass through the needle tube 120 and enter the main pipe 110. In the arrangement, the air pressure adjusting device 130 can be a small air pump. In other arrangements, the air pressure adjusting device 130 can be various other types of devices as the suction power mechanism, depending on the functional requirements for the absorption and recovering of the magnetic particle, which is not limited thereto.

As shown in FIG. 1, in the present arrangement, the recovery container 140 is connected to the main pipe 110 and is disposed between the first end and the second end of the main pipe 110 to receive and accommodate the magnetic particle 200 when the magnetic particle 200 enters the main pipe 110. In particular, the recovery container 140 may be designed to have a handle profile to facilitate the operator to hold it. Also, the connection position of the recovery container 140 with the main pipe 110 is disposed close to the second end of the main pipe 110. In other arrangements, the recovery container 140 of the present arrangement may be replaced with other structures to accommodate the magnetic particle 200. Alternatively, it is possible to omit the separate receiving structure, and the magnetic particle 200 may be accommodated in the main pipe 110, which are not limited thereto.

As shown in FIG. 1, in the present arrangement, an electromagnetic device is disposed on the main pipe 110 to form a magnetic field in the main pipe 110 to provide a moving force to the magnetic robot in the main pipe 110. Specifically, the electromagnetic device may include at least an electromagnetic coil 150 disposed around the outer circumference of the main pipe 110. Also, the electromagnetic device is disposed between the first end of the main pipe 110 and the recovery container 140 to move the magnetic particle 200 absorbed into the main pipe 110 into the recovery container 140. In other arrangements, the electromagnetic coil 150 may be replaced by other structures or components to provide a moving force to the magnetic particle 200 in the main pipe 110, or the above-mentioned moving force may be provided by other principles than electromagnetic methods, which are not limited thereto.

It should be noted that, in other exemplary arrangements of the present disclosure, the above-mentioned recovery container 140 and the electromagnetic device are not essential structures, and it is not necessary to provide both of them. For example, when only the recovery container 140 is provided, the recovery container 140 may be disposed substantially at a position between the first end and the second end of the main pipe 110 to receive and accommodate the magnetic particle 200 when magnetic particle 200 enters the main pipe 110. For another example, when only the electromagnetic device is provided, the electromagnetic device may be disposed substantially in the main pipe 110 to form a magnetic field in the main pipe 110 to provide a moving force to the magnetic particle 200 in the main pipe 110.

As described above, the design of the recovery device 100 provided by the present disclosure can make the recovering of the magnetic particle 200 from the vitreous body 300 (liquid working environment) more reliable and convenient, and avoid damage to the retinal macula or lens after, for example, an ablation procedure on the vitreous body 300, or avoid the risk of postoperative cataract after a vitrectomy.

It should be noted herein that the recovery device 100 illustrated in the drawings and described in this specification is only one example of many types of recovery devices 100 that are capable of employing the principles of the present disclosure. It should be clearly understood that the principles of the present disclosure are in no way limited to any detail of the recovery device 100 illustrated in the drawings or described in this specification or any component of the recovery device 100.

Accordingly, the recovery device 100 provided by the present disclosure can realize the adsorption of the magnetic robot by the magnetic needle tube 120, and simultaneously control the air pressure in the main pipe 110 and the needle tube 120 through the air pressure adjusting device 130, thus realizing the recovering of the magnetic robot. Based on the above solution of the present disclosure, direct damage to the retinal macula and lens caused by ablation of the vitreous body 300, or ocular lesion indirectly caused by the vitrectomy, can be avoided in the process of recovering the magnetic robot from the vitreous body 300.

Figure 2:
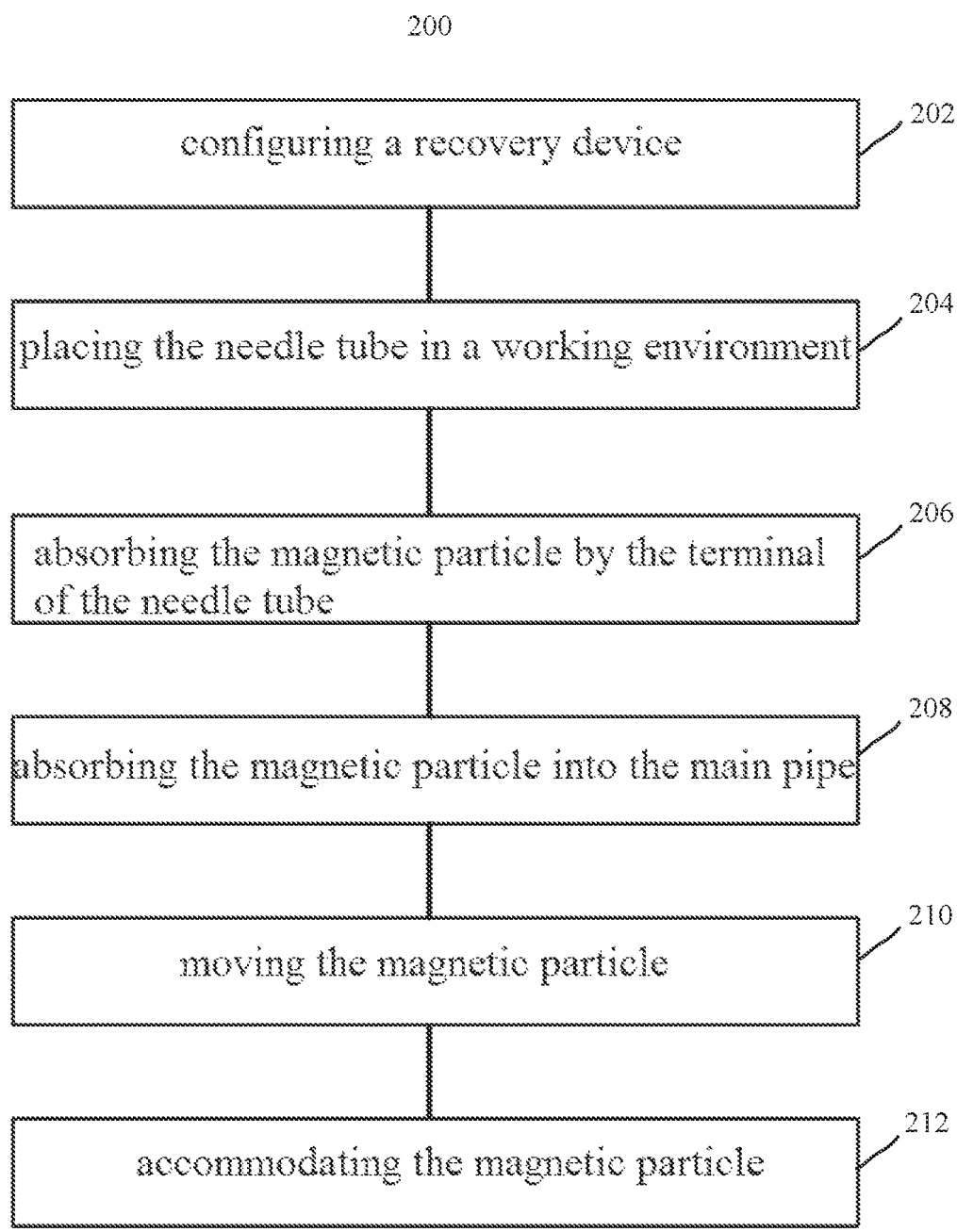
FIG. 2 is a flow chart of a method for recovering a magnetic particle according to an exemplary arrangement.

As shown in FIG. 2, in conjunction with the above description of an arrangement of the recovery device provided by the present disclosure, an exemplary arrangement of a method 200 for recovering a magnetic robot provided by the present disclosure will be described in detail below. The recovering method of the present arrangement is mainly used for recovering a magnetic particle from a vitreous body (liquid working environment) of a human eye, but is not limited to the recovering of other types of magnetic robots from other working environments with this method.

As shown in FIG. 2, the method 200 for recovering a magnetic robot by above mentioned recovery device provided by the present disclosure mainly includes the following blocks 202, 204, 206, 208, 210, and 212.

Block 202 includes configuring a recovery device. The recovery device includes a main pipe, a needle tube connected to a first end of the main pipe and an suction power mechanism. In some arrangements, the terminal of the needle tube away from the main pipe is magnetic.

Block 204 includes placing at least a part of the needle tube in a working environment of the magnetic robot that is to be adsorbed by the magnetic terminal of the needle tube. Such an operation may be referred to as a magnetic absorption.

Block 206 includes absorbing the magnetic particle by the magnetic terminal of the needle tube.

Block 208 includes absorbing the magnetic particle into the main pipe by the suction power mechanism. Such an operation may be referred to as a recovering process.

Further, as shown in FIG. 2, on the basis of "configuring a recovery device", "magnetic absorption" and "recovering", the method for recovering a magnetic robot may further include the following:

Block 210 includes moving the magnetic particle. Specifically, a magnetic field is formed by an electromagnetic device, and the magnetic robot is controlled to move in the main pipe by the action of the magnetic field.

Block 212 includes accommodating the magnetic particle. Specifically, a recovery container is connected to the main pipe. When the magnetic robot enters the main pipe, the magnetic robot is moved to the recovery container for storage.

It is understood that the above-mentioned "moving" and "accommodating" are not necessary blocks of the method for recovering a magnetic robot, and either of them can be separately or completely canceled, which is not limited thereto.

For example, on the basis of "configuring a recovery device", "magnetic absorption" and "recovering", the method for recovering a magnetic robot may further include the following operations:

Moving: a magnetic field is formed by an electromagnetic device, and the magnetic robot is controlled to move in the main pipe by the action of the magnetic field; or Accommodating: a recovery container is connected to the main pipe. When the magnetic robot enters the main pipe, the magnetic robot is moved to the recovery container for storage.

Accordingly, the method for recovering a magnetic robot provided by the present disclosure can realize efficient recovering of the magnetic robot by using a recovering tool such as the above described recovery device to magnetically absorb a magnetic robot and generate an instantaneous negative pressure for recovering the magnetic robot. The present disclosure is applicable to the recovering of a magnetic robot in a human eye environment, especially in a vitreous environment, to avoid direct damage to the human eye and indirectly caused eye lesions.

The present disclosure has been described with reference to a few exemplary arrangements, and it is understood that the terms used are illustrative and exemplary and not restrictive. The present disclosure may be embodied in a variety of forms without departing from the spirit or scope of the present disclosure. It is to be understood that the above-described arrangements are not limited to the details. All changes and modifications that come within the scope of the claims or the equivalents thereof are intended to be covered by the appended claims.

What is claimed is:

1. A recovery device for recovering a magnetic particle, comprising:
    a main pipe;
    a needle tube connected to a first end of the main pipe, and a terminal of the needle tube away from the main pipe is magnetic for adsorbing the magnetic particle to the terminal of the needle tube;
    an air pump connected to a second end of the main pipe and configured to absorb the magnetic particle attached on the terminal of the needle tube into the main pipe by applying a negative pressure in the main pipe; and
    a recovery container connected to the main pipe and disposed between the first end and the second end of the main pipe for accommodating the magnetic particle when the magnetic particle enters the main pipe, wherein the recovery container is designed to have a handle profile.

2. The recovery device according to claim 1, wherein a material of the main pipe is non-metal.

3. The recovery device according to claim 1, wherein a material of the main pipe is a transparent material.

4. The recovery device according to claim 1, wherein a material of the main pipe is non-metal and is a transparent material.

5. The recovery device according to claim 1, wherein a material of the needle tube is metal.

6. The recovery device according to claim 1, wherein a material of the terminal of the needle tube is a permanent magnet metal.

7. The recovery device according to claim 1, wherein a material of the needle tube is metal, and a material of the terminal of the needle tube is permanent magnet metal.

8. The recovery device according to claim 1, wherein the needle tube has a diameter less than or equal to 1 mm.

9. The recovery device according to claim 1, further comprising an electromagnetic device,
    wherein the electromagnetic device is disposed on the main pipe to form a magnetic field in the main pipe to provide a moving force to the magnetic particle in the main pipe.

10. The recovery device according to claim 9, wherein the electromagnetic device comprises at least an electromagnetic coil; and
    the electromagnetic coil is disposed around an outer circumference of the main pipe.

11. The recovery device according to claim 9, wherein the electromagnetic device is disposed between the first end of the main pipe and the recovery container.

12. The recovery device according to claim 1, wherein the needle tube is integrally formed with the main pipe.

13. The recovery device according to claim 1, wherein a portion of the main pipe proximate to the first end is substantially in a curved shape, and the curved shape is a gooseneck-like shape or an arc shape.

14. A method for recovering a magnetic particle by a recovery device, the recovery device comprises:
    a main pipe;
    a needle tube connected to a first end of the main pipe, and a terminal of the needle tube away from the main pipe is magnetic for adsorbing a magnetic particle to the terminal of the needle tube;
    an air pump connected to a second end of the main pipe and configured to absorb the magnetic particle attached on the terminal of the needle tube into the main pipe by applying a negative pressure in the main pipe; and
    a recovery container connected to the main pipe and disposed between the first end and the second end of the main pipe for accommodating the magnetic particle when the magnetic particle enters the main pipe, wherein the recovery container is designed to have a handle profile;
    the method for recovering a magnetic particle comprising:
    magnetic absorption, placing at least a part of the needle tube in a working environment of a magnetic particle, and the magnetic particle is to be absorbed by the terminal of the needle tube;
    absorbing the magnetic particle into the main pipe by the air pump; and
    connecting the recovery container to the main pipe, and when the magnetic particle enters the main pipe, the magnetic particle is moved to the recovery container for storage.

15. The method for recovering a magnetic particle according to claim 14, further comprising:
    forming a magnetic field by an electromagnetic device, and the magnetic particle is controlled to move in the main pipe by the action of the magnetic field.

* * * * *